United States Patent [19]

Sekiguchi

[11] Patent Number: 4,821,117
[45] Date of Patent: Apr. 11, 1989

[54] ENDOSCOPIC SYSTEM FOR PRODUCING FLUORESCENT AND VISIBLE IMAGES

[75] Inventor: Tadashi Sekiguchi, Utsunomiya, Japan

[73] Assignee: Kabushiki Kaisha Toshiba, Kawasaki, Japan

[21] Appl. No.: 119,905

[22] Filed: Nov. 10, 1987

[30] Foreign Application Priority Data

Nov. 12, 1986 [JP] Japan ................... 61-267798

[51] Int. Cl.$^4$ .................................. H04N 7/18
[52] U.S. Cl. .......................... 358/98; 128/6
[58] Field of Search .............. 358/98, 93; 128/4, 6; 250/363 S, 458.1

[56] References Cited

U.S. PATENT DOCUMENTS 3,835,246 9/1974 Muller et al. ................. 358/93
4,327,738 5/1982 Green et al. ................. 358/98 X
4,595,014 6/1986 Barrett et al. ............. 250/363 S X Primary Examiner—James J. Groody
Assistant Examiner—Victor R. Kostak
Attorney, Agent, or Firm—Foley & Lardner, Schwartz, Jeffery, Schwaab, Mack, Blumenthal & Evans

[57] ABSTRACT

An endoscopic system irradiates an object to be inspected and applied with a fluorescent material with visible radiation to obtain a visible radiation image of the object and with excitation radiation to obtain a fluorescent image thereof. The images thus obtained being alternately inputted into a television camera and displayed simultaneously on a display unit according to outputs from the television camera. The endoscopic system comprises an emission switch for irradiating the object alternately with the visible radiation and the excitation radiation, a first frame memory for storing the visible radiation image from the television camera, a second frame memory for storing the fluorescent image from the television camera, an image signal switch for alternately inputting the images from the television camera into the first and second frame memories, an image processing and displaying unit for processing and displaying the images from the first and second frame memories, and a central controlling portion for synchronously controlling the emission switch and the image signal switch, readout operations of the first and second frame memories, and the image processing and displaying unit to simultaneously display both the images on the display unit.

9 Claims, 6 Drawing Sheets

ENDOSCOPIC SYSTEM FOR PRODUCING FLUORESCENT AND VISIBLE IMAGES

BACKGROUND OF THE INVENTION

1. Field of the Invention

The present invention relates to an endoscopic system for photographing and inspecting the state of a body cavity or an internal organ of a human body, and particularly to an endoscopic system which can simultaneously display a visible radiation image and a fluorescent image of the internal organ.

2. Description of the Prior Art

In endoscopic system for photographing and inspecting the state of an internal organ of a human body, there are two types, one obtaining an image of the internal organ by irradiating the internal organ with visible radiation, and another obtaining a fluorescent image (a contrast image) of the internal organ by applying a fluorescent material to the internal organ and irradiating the internal organ with excitation radiation.

An affected part such as a cancer of the internal organ may be identified by comparing the visible radiation image of the internal organ with the fluorescent image thereof.

According to a conventional endoscopic system of any one of the above-mentioned types, a television camera is attached to an eye contacting portion of a fiberscope, and an optical guide fiber for guiding a beam from an external radiation source is arranged at a portion of the fiber scope to be inserted into the body.

The endoscopic system for obtaining the visible radiation image is equipped with a normal white light source emitting visible radiation only, while the endoscopic system for obtaining the fluorescent image is equipped with a laser which emits light for exciting fluorescent materials only.

The endoscopic system for the visible radiation image and the endoscopic system for the fluorescent image are arranged as completely separated apparatuses.

Due to this, in inspecting an internal organ of the human body, separate operations for the two systems shall be achieved to obtain the visible radiation image and the fluorescent image of the internal organ. If both of the images can simultaneously be displayed on a same display unit to compare the visible radiation image with the fluorescent image, it will be easy and sure to identify an affected part of the internal organ.

However, according to the conventional endoscopic systems, the system for the visible radiation image and the system for the fluorescent image are completely separated as two systems so that the visible radiation image and the fluorescent image cannot be displayed at the same time on the same display unit.

SUMMARY OF THE INVENTION

In considering the above, an object of the present invention is to provide an endoscopic system which can simultaneously display a visible radiation image and a fluorescent image of an internal organ on a same display unit to easily and securely identify an affected part of the internal organ.

In order to accomplish the object, the present invention provides an endoscopic system in which an object to be inspected and applied with a fluorescent material is irradiated with visible radiation to obtain a visible radiation image of the object and irradiated with excitation radiation to obtain a fluorescent image thereof. The visible radiation and fluorescent images thus obtained are alternately inputted into an image pickup device and displayed simultaneously on a displaying device according to outputs from the image pickup device. For that, the endoscopic system comprises an emission switching device for irradiating the object alternately with the visible radiation and the excitation radiation, a first storing device for storing the visible radiation image supplied from the image pickup device, a second storing device for storing the fluorescent image supplied from the image pickup device, an image signal switching device for alternately supplying the visible radiation image and the fluorescent image from the image pickup device into the first storing device and the second storing device, an image displaying device for processing and displaying the images from the first and second storing device, and a controlling device for synchronously controlling the switching operation of the emission switching device and the image signal switching device and for controlling the readout operation of the first and second storing device as well as the operation of the image displaying device so as to simultaneously display the visible radiation image and the fluorescent image on the image displaying device.

According to the endoscopic system of the present invention, after a fluorescent material is applied to an object to be inspected, the emission switching device and the image signal switching device are synchronously switched by the controlling device such that, when the object is irradiated with visible radiation, a visible radiation image of the object is inputted into the image pickup device to store outputs thereof in the first storing device. On the other hand, when the object is irradiated with excitation radiation, a fluorescent image of the object is inputted into the image pickup device to store outputs thereof in the second storing device under the switching control of the controlling device. The visible radiation and fluorescent images stored in the first and second storing device are simultaneously read under the control of the controlling device and processed by the image displaying device so that the visible radiation and fluorescent images are simultaneously displayed on the displaying device.

BRIEF DESCRIPTION OF THE DRAWINGS

These and other objects, features and advantages of the present invention will become apparent from the following description of preferred embodiments taken in conjunction with the accompanying drawings in which.

DETAILED DESCRIPTION OF THE PREFERRED EMBODIMENTS

Figure 1:
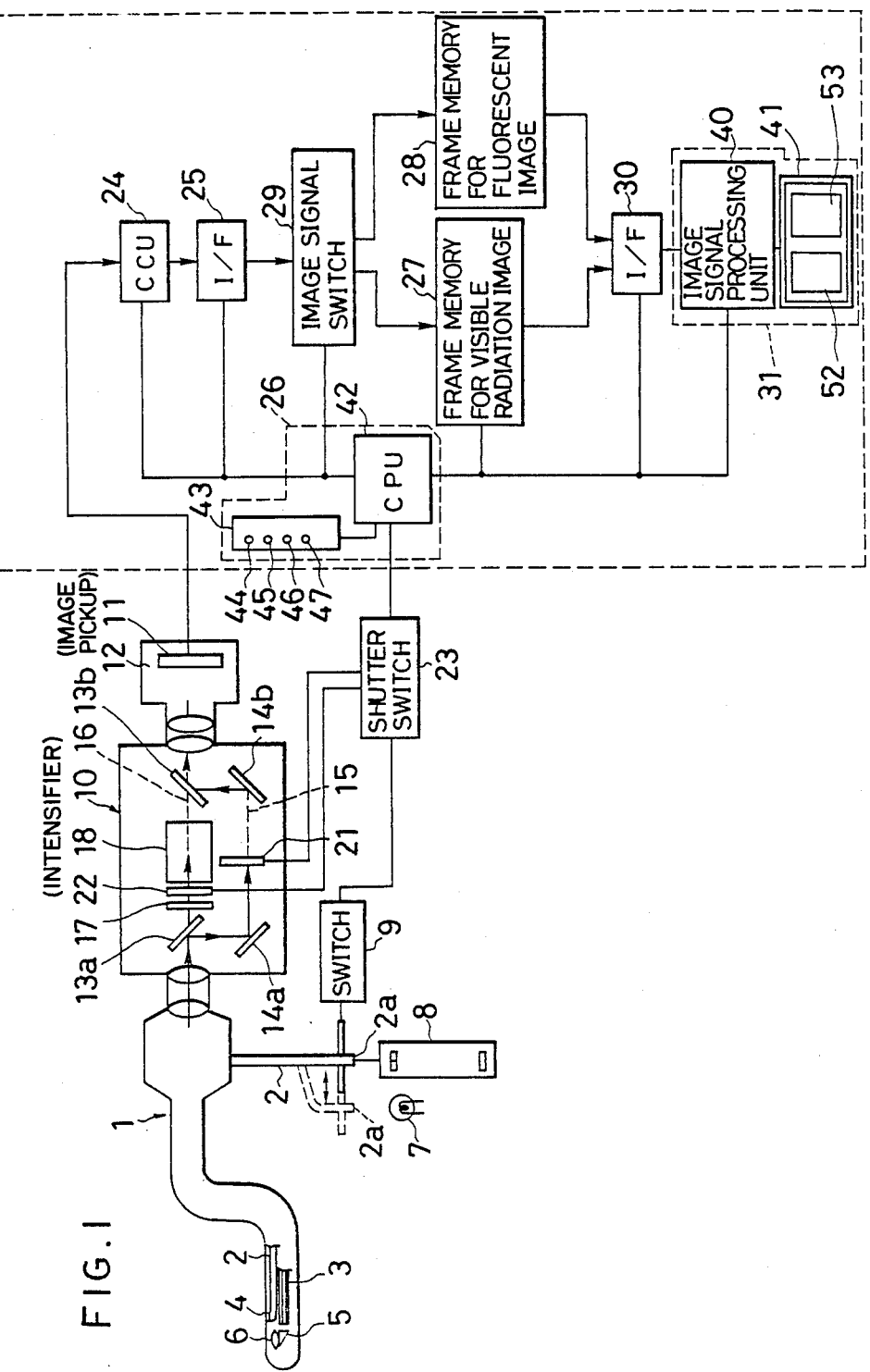
FIG. 1 is a block diagram showing an embodiment of an endoscopic system according to the present invention.

FIG. 1 shows an endoscopic system according to the present invention, which comprises a fiberscope 1 in which an optical guide fiber 2 for guiding light from a light source, and an optical fiber 3 for transmitting optical images are disposed. At one end of the optical guide fiber 2 which is to be inserted into a body, there are arranged a radiation window 4, a prism 5 and an objective lens 6. The prism 5 and objective lens 6 are for the optical fiber 3.

The other end of the optical guide fiber 2 is an incident end face 2a facing the light source. The light source comprises a white light source 7 for emitting visible radiation and a laser 8 for emitting excitation radiation for fluorescent materials.

The laser 8 oscillates a laser beam whose wavelength corresponds to an absorption spectrum (FIG. 2) of a fluorescent material to be used as a contrast medium which is applied to the object to be inspected.

The incident end face 2a of the optical guide fiber 2 is positioned by an emission switching means which comprises a switch 9, such that the incident end face 2a faces the white light source 7 or the laser 8.

The fiberscope 1 is connected to a television camera (an image pickup means) 12 using a solid-state image pickup element 11, through an image intensifier portion 10.

The image intensifier portion 10 comprises a light path 15 for visible radiation images and a light path 16 for fluorescent images, the light paths being formed with two half-mirrors 13a and 13b and two mirrors 14a and 14b. The light path 16 for fluorescent images is provided with a sharp-cut filter 17 and an image intensifier 18 for amplifying fluorescent images.

Figure 2A:
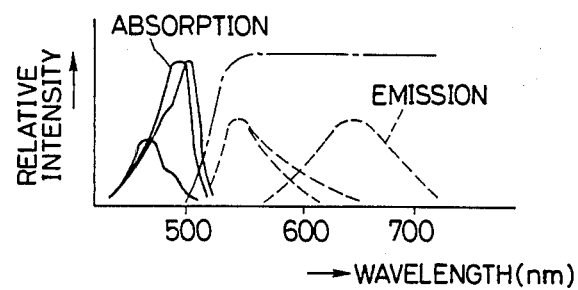
FIGS. 2(A) to 2(D) are characteristic curves showing the absorption and emission spectra of fluorescent materials adopted for the embodiment shown in FIG. 1.
Figure 2B:
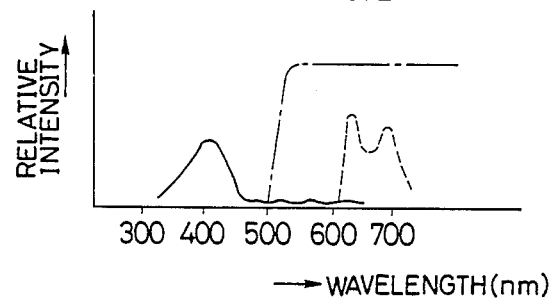
Figure 2C:
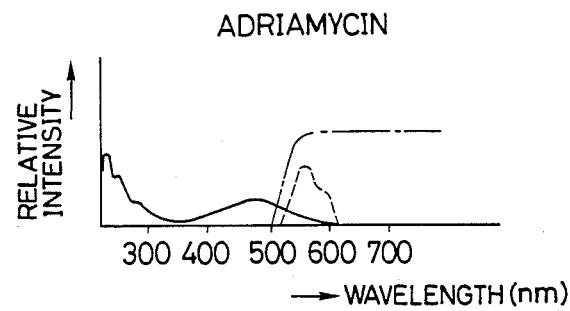
Figure 2D:
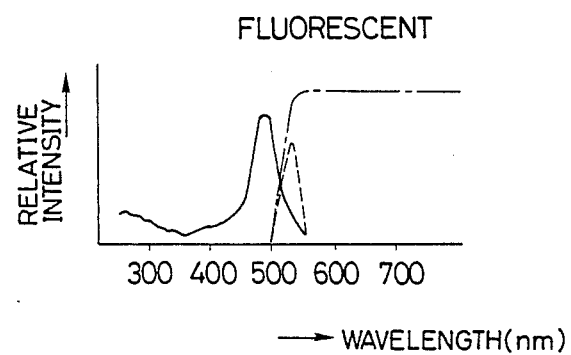

A fluorescent material to be applied to a body will be, as shown in FIGS. 2(A) to 2(D), acridine orange (FIG. 2(A)), hematoporphyrin derivative (FIG. 2(B)), adriamycin (FIG. 2(C)), or fluorescent (FIG. 2(D)).

In characteristic curves shown in FIGS. 2(A) to 2(D), continuous lines represent absorption spectra and dashed lines emission spectra.

As shown in the figures, peaks of the absorption spectra of the respective fluorescent materials appear on the shorter side of a wavelength of 500 nm, and peaks of the fluorescent spectra on the longer side of the wavelength of 500 nm. Accordingly, the sharp-cut filter 17 will be one which can cut light having wavelengths of 500 nm and shorter.

The sharp-cut filter 17 is provided with, for instance, a coat of a multiple deposition film.

The image intensifier portion 10 further comprises shutters 21 and 22 for alternately opening and closing the light path 15 for visible radiation images and the light path 16 for fluorescent images. The shutters 21 and 22 are driven by a shutter switch 23 to open and close the light paths 15 and 16 alternately.

The shutters 21 and 22 and the shutter switch 23 constitute an incident light switching means for inputting a visible radiation image and a fluorescent image one after the other into the television camera 12.

The shutter switch 23 is connected to the switch 9 constituting the emission switching means. The shutter switch 23 is controlled by a controlling means to be described later, and the switch 9 is also controlled by the controlling means through the shutter switch 23.

The television camera 12 is connected to a camera controlling unit 24 which is connected to an image signal switch 29 through an interface 25. The image signal switch 29 is controlled by a central controlling portion 26 having a CPU 42.

The central controlling portion 26 has a control line connected to the shutter switch 23.

A first frame memory (a first storing means) 27 for storing visible radiation image signals and a second frame memory (a second storing means) 28 for storing fluorescent image signals are connected to the image signal switch 29 constituting an image signal switching means. The first frame memory 27 and the second frame memory 28 are connected to a displaying means 31 through an interface 30. The displaying means 31 comprises an image signal processing unit 40 for processing the visible radiation image signals and the fluorescent image signals from the interface 30, and a display unit 41 for displaying image signals processed by the image signal processing unit 40. The image signal processing unit 40 processes image signals from the interface 30 according to an instruction signal sent from the central controlling portion 26, such that the visible radiation image and the fluorescent image are simultaneously displayed on the display unit 41.

The central controlling portion 26 has an input switch portion 43 connected to the CPU 42. The input switch portion 43 includes a visible radiation image displaying switch 44 which instructs to display only a visible radiation image; a fluorescent image displaying switch 45 which instructs to display only a fluorescent image; a visible radiation image/fluorescent image displaying switch 46 which instructs to simultaneously display a visible radiation image and a fluorescent image; and a visible radiation image/fluorescent intensity contour lines displaying switch 47 which instructs to display a visible radiation image and fluorescent intensity contour lines to be overlapped each other. According to an operator's operation of the input switch portion 43, the CPU 42 controls the shutter switch 23, image signal switch 29, first frame memory 27 for visible radiation image, second frame memory 28 for fluorescent image, and image signal processing unit 40 as explained later.

The operation of the above-mentioned system will be described.

An internal organ to be inspected is applied with any one of the fluorescent materials having characteristics shown in FIGS. 2(A) to 2(D).

Supposing that an operator operates the visible radiation image/fluorescent image displaying switch 46 of the input switch portion 43, and inserts one end of the fiberscope 1 into the internal organ to take a visible radiation image of the internal organ. Then, according to an instruction signal from the input switch portion 43 to simultaneously display the visible radiation image and fluorescent image, the CPU 42 sends synchronous control signals to the shutter switch 23 and the image signal switch 29. When the shutter switch 23 is activated, the switch 9 is driven to position the incident end face 2a of the optical guide fiber 2 to face the white light source 7. The shutters 21 and 22 are operated to close the light path 16 for fluorescent images and open the light path 15 for visible radiation images. At the same time, the image signal switch 29 connects the first frame memory 27 to the interface 25.

Then, visible radiation from the white light source 7 irradiates the object to be inspected through the radiation window 4. Light reflected by the object is collected by the objective lens 6 to form an image on an incident end face of the optical fiber 3. The visible radiation image is transmitted through the optical fiber 3 and the optical path 15 and made incident into the television camera 12. The television camera 12 photographs the visible radiation image and outputs the same.

The outputted visible radiation image from the television camera 12 is inputted into the image signal switch 29 through the camera controlling unit 24 and the interface 25, and stored in the first frame memory 27 which is in connection with the interface 25 under the control of the CPU 42.

After the above-mentioned photographing operation, the CPU 42 sends another controlling signal to switch the incident end face 2a of the optical guide fiber 2 to face the laser 8, and to close the optical path 15 for visible radiation images and open the optical path 16 for fluorescent images. Further, the second frame memory 28 is connected to the interface 25 through the image signal switch 29.

Then, excitation radiation from the laser 8 irradiates the object through the radiation window 4. The fluorescent material is excited by the excitation radiation and emits fluorescent to form, through the objective lens 6, a fluorescent image (a contrast image) on the incident end face of the optical fiber 3. At this time, excitation radiation reflected by the object is made incident, together with the fluorescent image, into the incident end face of the optical fiber 3.

The fluorescent image including the reflected excitation radiation is transmitted through the optical fiber 3 to reach the optical path 16 for fluorescent images. Then, the sharp-cut filter 17 cuts the reflected excitation radiation, and only the fluorescent image is intensified to a required level by the image intensifier 18 and made incident into and photographed by the television camera 12 which outputs the photographed fluorescent image.

The outputted fluorescent image from the television camera 12 is inputted into the image signal switch 29 through the camera controlling unit 24 and the interface 25, and stored in the second frame memory 28 which is in connection with the interface 25 under the control of the CPU 42.

After that, the visible radiation image signals and the fluorescent image signals stored in the first and second frame memories 27 and 28 respectively are simultaneously read under the control of the CPU 42 and sent to the image signal processing unit 40 through the interface 30. The image signal processing unit 40 processes the image signals from the interface 30 and sends the processed signals to the display unit 41, such that the visible radiation image and the fluorescent image are simultaneously displayed on the display unit 41. Then, the display unit 41 displays the images 52 and 53. The image displaying means 31 is constituted by the image signal processing unit 40 and the display unit 41.

By comparing the simultaneously displayed images with each other, an affected part on the internal organ can easily and securely be identified.

Figure 3:
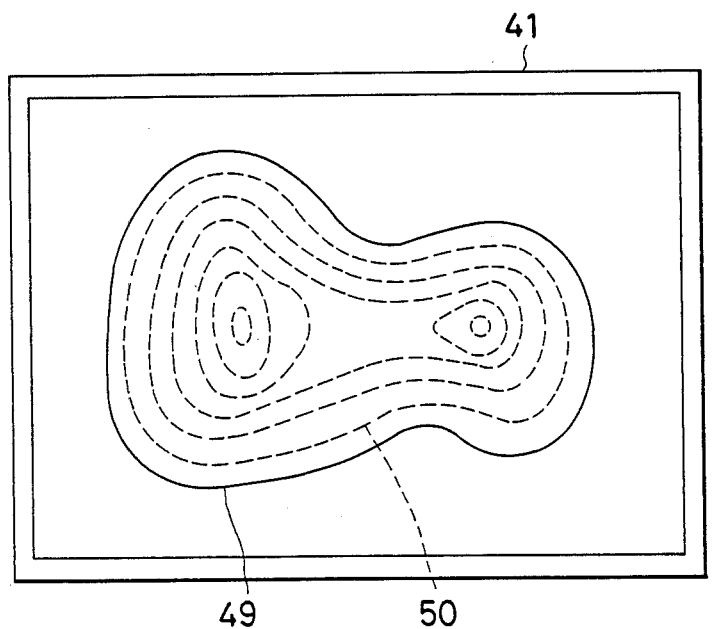
FIG. 3 is a view showing a state that a visible radiation image and fluorescent intensity contour lines overlap each other on a display unit shown in FIG. 1.

Supposing that the operator operates the visible radiation image/fluorescent intensity contour lines displaying switch 47 of the input switch portion 43. In this case, the flow of image signals up to the interface 30 and the switching operation accompanied are the same as those in the operation of the visible radiation image/fluorescent image displaying switch 46, and operations thereafter differ from them, for which an explanation will be made. The image signal processing unit 40 receives image signals from the interface 30 and a control signal from the CPU 42 to compute the fluorescent intensity contour lines of a fluorescent image, and processes the image signals such that the fluorescent intensity contour lines are overlapped on a visible radiation image on the display unit 41. The processed image signals are supplied to the display unit 41. Therefore, as shown in FIG. 3, a visible radiation image 49 and the fluorescent intensity contour lines are overlapped each other on the display unit 41.

Figure 4:
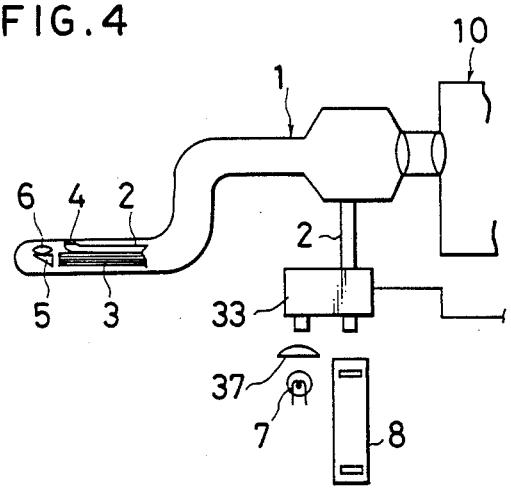
FIGS. 4 and 5 are views showing the constitution of a modification of an emission switching means shown in FIG. 1.
Figure 5:
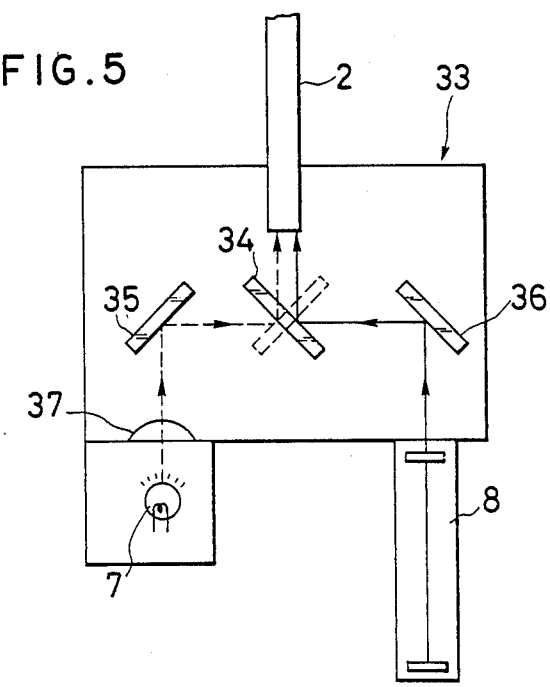

FIGS. 4 and 5 show a modified embodiment of the present invention.

This modified embodiment relates to a modification of the emission switching means of the first embodiment (FIG. 1).

According to the modification, an emission switching means 33 comprises a rotary mirror 34 as shown in FIG. 5. The rotary mirror 34 may be a single side reflecting mirror or a double side reflecting mirror. The rotary mirror 34 is connected to a motor (not shown) which rotates for a predetermined number of revolutions according to a switching signal from the shutter switch 23 shown in FIG. 1 to turn the rotary mirror 34.

On both sides of the rotary mirror 34, there are disposed reflecting mirrors 35 and 36, and, at locations corresponding to the reflecting mirrors 35 and 36, there are arranged a white light source 7 and a laser 8. In FIG. 5, the emission switching means 33 is provided with a condenser lens 37 for collecting light from the white light source and guiding the light toward the reflecting mirror 35.

When the rotary mirror 34 is located as indicated by a continuous line in FIG. 5, excitation radiation oscillated by the laser 8 is reflected by the reflecting mirror 36 and the rotary mirror 34, made incident into an incident end face of the optical guide fiber 2, and irradiates an object to be inspected.

When the rotary mirror 34 is rotated to a position indicated by a dashed line in FIG. 5, visible radiation from the white light source 7 is collected by the condenser lens 37, reflected by the reflecting mirror 35 and the rotary mirror 34, made incident into the incident end face of the optical guide fiber 2, and irradiates the object to be inspected.

By using the double side reflecting mirror as the rotary mirror 34, the rotational controlling amount of the rotary mirror 34 will be reduced to a half compared to one realized by the single side reflecting mirror.

With this emission switching means 33 of the modification, a switching operation between visible radiation and excitation radiation will smoothly be carried out with relatively simple constitution.

Figure 6:
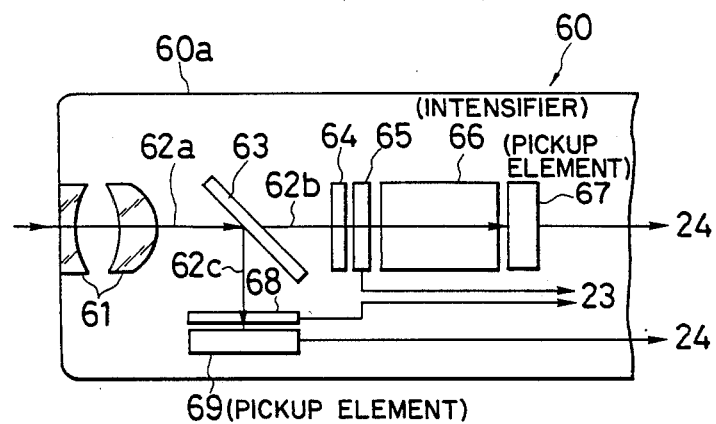
FIGS. 6 and 7 are diagrams showing modifications of a scope of the endoscopic system according to the present invention.
Figure 7:
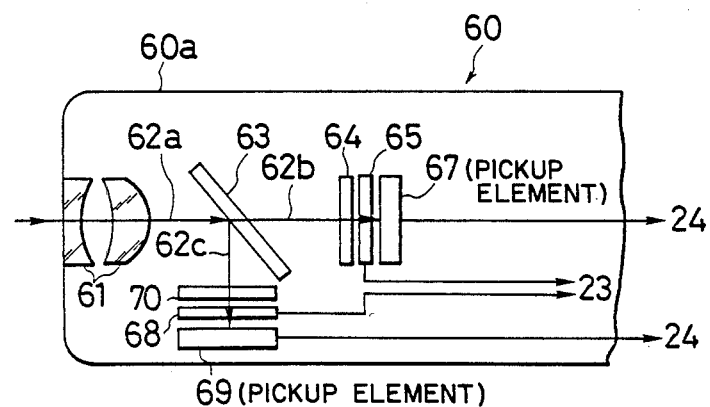

FIGS. 6 and 7 are views showing a modification of the scope of the endoscopic system according to the present invention.

According to this modification, a solid-state image pickup element and an image intensifier portion, which are disposed outside a scope according to the first embodiment, are arranged at a front end portion of the scope. FIG. 6 shows the constitution of an end of a scope incorporating a low-sensitivity solid-state image pickup element, while FIG. 7 shows the constitution of an end of a scope incorporating a high-sensitivity solid-state image pickup element.

Referring to the modification shown in FIG. 6, a front end portion 60a of a scope 60 incorporates lenses 61. A half-mirror 63 is disposed to face incident light 62a from the lens 61. To face transmitted light 62b passed through the half-mirror 63, there are successively disposed a sharp-cut filter 64, a shutter 65, an image intensifier 66, and a solid-state image pickup element 67 for fluorescent images. At a position facing reflected light 62c reflected by the half-mirror 63, there are successively disposed a shutter 68 and a solid-state image pickup element 69 for visible radiation images. Image signals generated by the solid-state image pickup elements 69 and 67 are supplied to the camera controlling unit 24 shown in the first embodiment. The shutters 65 and 68 are connected to the shutter switch 23 shown in the first embodiment such that they are driven and switched according to driving signals from the shutter switch 23.

Therefore, based on the controlling operation of the CPU 42 shown in the first embodiment, image signals for a visible radiation image and image signals for a fluorescent image are alternately outputted from the solid-state image pickup elements 69 and 67.

Other constitution and operation of this modification are the same as those of the first embodiment.

The modification shown in FIG. 7 uses the high-sensitivity solid-state image pickup element. This modification has no image intensifier 66 used in the above-mentioned modification, and is provided with an ND filter 70 between a shutter 68 and a half-mirror 63. Other constitution and operation of this modification are the same as those of the above-mentioned modification.

Although the above-mentioned embodiments have been explained to handle frozen images, they can display visible radiation images and fluorescent images simultaneously as real images. Namely, a frame of visible radiation image signals and a frame of fluorescent image signals are simultaneously read out of the first and second frame memories 27 and 28 with one blank frame being inserted between the successive reading operations. The read image signals are processed by the image signal processing unit 40 such that two frames each for both the images are generated from the read image signals and displayed. Thus, both the images are displayed on the display unit 41 as continuous real images.

In summary, according to the present invention, a fluorescent material is preliminary applied to an object to be inspected, and the controlling means sends control signals to synchronously switch the emission switching means, incident light switching means, and image signal switching means. When the object is irradiated with visible radiation, a visible radiation image is inputted into the image pickup means, and outputs from the image pickup means are stored in the first storing means. On the other hand, when the object is irradiated with excitation radiation, a fluorescent image is inputted into the image pickup means, and outputs from the image pickup means are stored in the second storing means. The visible radiation image and the fluorescent image stored in the first and second storing means respectively are simultaneously read therefrom by the controlling means and displayed on the displaying means simultaneously. Therefore, an affected part on the object to be inspected is easily and securely identified.

Various modifications will become possible for those skilled in the art after receiving the teachings of the present disclosure without departing from the scope thereof.

What is claimed is:

1. An endoscopic system for simultaneously displaying a visible radiation image and a fluorescent image of an object to which has been applied, for inspection, a fluorescent material, comprising:
   first storing means for storing the visible radiation image of the object;
   second storing means for storing the fluorescent image of the object;
   means for irradiating the object with visible radiation and excitation radiation alternately to obtain a visible radiation image and a fluorescent image of the object;
   means for supplying the visible radiation image and the fluorescent image to the first and second storing means, respectively;
   means for intensifying the fluorescent image to a predetermined level;
   image displaying means for processing and displaying the images from the first and second storing means; and
   controlling means for controlling the irradiating means, first and second storing means, and image displaying means such that the visible radiation image and the fluorescent image are simultaneously displayed on the image displaying means.

2. The endoscopic system as claimed in claim 1, wherein said irradiating and supplying means comprises:
   visible radiation emitting means for irradiating the object with visible radiation to obtain the visible radiation image of the object;
   excitation radiation emitting means for irradiating said object with excitation radiation to obtain the fluorescent image of the object;
   emission switching means for irradiating the object with the visible radiation and the excitation radiation alternately;
   image pickup means for picking up the visible radiation image and fluorescent image of the object; and
   image signal switching means for supplying the visible radiation image and the fluorescent image from said image pickup means to said first storing means and said second storing means, respectively.

3. The endoscopic system as claimed in claim 2, wherein said controlling means controls said emission switching means and said image signal switching means such that the visible radiation image and the fluorescent image are inputted in said first and second storing means, respectively, said first and second storing means controlled such that the visible radiation image and the fluorescent image are simultaneously read out from said first and second storing means controlled, and said image displaying means such that the visible radiation image and the fluorescent image from said first and second storing means are simultaneously displayed on said image displaying means.

4. The endoscopic system as claimed in claim 2, further comprising an incident light switching means for alternately inputting the visible radiation image and the fluorescent image to said image pickup means.

5. The endoscopic system as claimed in claim 3, wherein said image displaying means comprises:
   a display unit for displaying images; and
   an image signal processing unit for processing image signals from said first and second storing means such that the visible radiation image and the fluorescent image are simultaneously displayed on the display unit.

6. The endoscopic system as claimed in claim 2, wherein said intensifying means comprises an image intensifier constructed to intensify the fluorescent image obtained by irradiating the object to be inspected with excitation radiation.

7. The endoscopic system of claim 1, in which the controlling means selectively causes the display on said image display means of the visible image, the fluorescent image, or both simultaneously.

8. An endoscopic system for simultaneously displaying a visible radiation image and a fluorescent image of an object to which has been applied, for inspection, a fluorescent material, comprising:
   first storing means for storing the visible radiation image of the object;
   second storing means for storing the fluorescent image of the object;
   visible irradiation means for irradiating the object with visible radiation;
   excitation irradiation means for irradiating the object with excitation radiation;
   emission switching means to alternately obtain a visible radiation image and a fluorescent image of the object;
   image signal switching means for supplying the visible radiation image and the fluorescent image from the emission switching means to the first and second storing means, respectively;
   image displaying means for processing and displaying the images from said first and second storing means; and
   controlling means for controlling the visible and fluorescent irradiating means, the first and second storing means, and the image display means, wherein the controlling means comprises:
   an input switch having at least a visible radiation image displaying switch that instructs the display unit to display only the visible radiation image, a fluorescent image displaying switch that instructs the display unit to display only the fluorescent image, and a visible radiation image/fluorescent image displaying switch that instructs the display unit to simultaneously display the visible radiation image and the fluorescent image; and
   a CPU connected to and controlling the input switch to provide the desired image or images.

9. The endoscopic system of claim 8, further including means for intensifying the fluorescent image to a predetermined level.

* * * * *